United States Patent [19]

Dinan et al.

[11] Patent Number: 5,324,738

[45] Date of Patent: Jun. 28, 1994

[54] DIAGNOSIS AND TREATMENT OF A DISORDER OF THE GASTROINTESTINAL TRACT

[75] Inventors: Timothy G. Dinan; Paul W. N. Keeling, both of Dublin, Ireland

[73] Assignee: Earlow Limited, Dublin, Ireland

[21] Appl. No.: 584,146

[22] Filed: Sep. 18, 1990

[51] Int. Cl.$^5$ .......................................... A61K 31/445
[52] U.S. Cl. ................................................... 514/325
[58] Field of Search .......................................... 514/325

[56] References Cited

U.S. PATENT DOCUMENTS 4,602,043 7/1986 Geho ................................... 514/646

FOREIGN PATENT DOCUMENTS 0092114 10/1983 European Pat. Off. .
0419237  3/1991 European Pat. Off. .

OTHER PUBLICATIONS

Chem Abst, 113:35190r (1990). Dinan et al.
Chem Abst, 92:34440h (1980). Golstein et al.
The Merck Index, Tenth Edition (1983). pp. 398 and 399.
Dorland's Illustrated "Medical Dictionary", 26th Ed., p. 413, 1985.
Van de Kar et al., Neuropharmacology, 28, 299–305, 1989.
Allen et al., Arzneimittel-Forschung, 24, 917–922, 1974.
Carroll, Brit.J.Psychiat. (1982), 140, 292–304.
Coppen et al, Brit.J.Psychiat. (1983), 142, 498–504.
Chaudhary et al, Quarterly Journal of Medicine, New Series XXXI, No. 123, Jul. 1962, 307–322.
Dinan et al, Scandinavian Journal of Gasteroenterology, 1990, 25, 541–544.
Dinan et al, Journal of Psychosomatic Research, 1990, 34, 575.
Gershon et al, Psychiatry Update vol. II, 1983.
Gomez et al, British Medical Journal, Jun. 4, 1977, 1451–1453.
Jiang et al, Gastroenterology 1988; 95:1265–71.
Klein, Gastroenterology 1988; 95:232–41.
Warner, Annals of Internal Medicine, vol. 59, No. 4, Oct. 1963, 464–476.
Talley et al, Annals of Internal Medicine, vol. 108, No. 6, pp. 865–879, 1988.
Delfia TM Prolactin Kit, LKB (Publisher) Oct. 19, 1986.
Read, 7–13, Scandinavian Journal of Gasteroenterology Supplement (1987).
Reylon et al., Indian Journal of Physiology and Pharmacology, 27, 342–344, 1983.
Kennedy et al., Gastroenterology, 66, 396–402, 1974.
Yatham et al., The Lancet, 1, No. 8652, 1447–1448, 1989.
Urban et al., Pharmacology Biochemistry & Behavior, 25, 457–462, 1986.
Hoyer, Journal of Receptor Research, 8, 59–81, 1988.
Kilbinger et al., The British Journal of Pharmacol., 85, 529–539, 1985.
N. W. Read, (1987) Functional Disorders of the Stomach and Small Bowel, Philadelphia, Saunders, pp. 7–13.

*Primary Examiner*—Zohreh A. Fay
*Attorney, Agent, or Firm*—Birch, Stewart, Kolasch and Birch

[57] ABSTRACT

Cyproheptadine (4-(5H-dibenzo[a,d] cyclohepten-5-ylidene)-1-methylpiperidine) for the treatment of non-ulcerative dyspepsia (NUD), more particularly NUD which is characterised by dysfunction of central 5-HT 1A receptors. Dysfunction of the central 5-HT 1A receptors can be diagnosed by an azaspirodecanedione-induced prolactin response which is distinguishable from that observed in a subject with peptic ulcer disease and/or inflammatory bowel disease. A suitable azaspirodecanedione for inducing the prolactin response is buspirone.

13 Claims, 3 Drawing Sheets

DIAGNOSIS AND TREATMENT OF A DISORDER OF THE GASTROINTESTINAL TRACT

BACKGROUND OF THE INVENTION

This invention relates to the therapy of irritable bowel syndrome (IBS), in particular, upper irritable bowel syndrome (non-ulcerative dyspepsia), and related conditions as hereinafter described.

Irritable bowel syndrome is the most common reason for referral to gastroenterology clinics and affects 10–12% of the whole population. To date, systematic efforts to determine its aetiology have proved fruitless. No consistent biochemical or physiological abnormalities have been demonstrated and many gastroenterologists describe it as a functional disorder, without an organic basis. IBS can be described as a condition of the gastrointestinal tract characterised by a disorder of the gut motility or rate of movement along the gastrointestinal tract which may be either delayed or increased. Accordingly, IBS is not characterised by any consistent abnormality in the gut.

The degree of psychological abnormality attributed to patients with IBS varies from study to study. At the inventors' clinic, using standardised diagnostic criteria (DSM-III) (American Psychiatric Association *Diagnostic and Statistical Manual of Mental Disorders*) (3rd Ed. Washington D.C.: APA), approximately 30% of IBS patients have been found to have psychiatric illness, whilst others using less rigorous diagnostic criteria suggest abnormality in over 80% of such patients (Chaudhury, N.A., and Truelove, S. C., Q. J. Med. 1962; 31:307-322). A more recent study by Gomez, J. and Dally, P. (B. M. J., 1977: 1; 1451-1453) again found that almost all patients have evidence of psychiatric illness, the most common diagnosis was depression, followed by anxiety states and hysterical conversion. The high level of obsessional traits in such patients has also been stressed.

A gastrointestinal syndrome consisting of early satiety, post-prandial fullness/bloating, belching, nausea and epigastric pain in the absence of significant organic pathology is well recognised and usually described as non-ulcerative dyspepsia (NUD) (see for example, Nyren, D. et al., 1987, J. Clin. Gastroenterol. 20, 896–900). Attempts to elucidate its aetiology have failed to produce consistent pathophysiological correlates and numerous psychological theories have been postulated to explain the symptoms. The terms pseudoulcer syndrome, pyloroduodenal irritability, functional dyspepsia, nervous dyspepsia and more recently upper irritable bowel syndrome have all been used. It has a prevalence of around 20% and an annual incidence of over 1%. It is a costly condition resulting in expensive investigations and the use of empiric treatments of healing peptic ulcers.

The sympathetic division of the autonomic nervous system has long been recognised as important in the control of gastrointestinal function. Noradrenergic (NA) $\alpha$-2 receptors in the hypothalamus form an important part of this network and recent research has demonstrated that these receptors have a significant influence on intestinal motility and transit time (Jiang, Q.I. et al. *Gastroenterology* 1988; 95: 1265-1271). The $\alpha$-2 agonist clonidine acting centrally produces a dose-dependent decrease in intestinal motility (Jiang, Q,I, et al. supra).

Serotonin is a monoamine which acts both as a transmitter in the gut and centrally in the brain. It plays an important role in regulating peristalsis and intestinal tone. Some cases of functional abdominal pain have been attributed to hyperserotoninaemia (Warner, R.P., Ann. Intern. Med. 1963;59: 464–76).

Research to date indicates that there are at least three types of 5-HT receptors, 5-HT 1, 5-HT 2 and 5-HT 3. The 5-HT 1 receptor is further subdivided into 5-HT 1A, 1B and 1C. These 5-HT 1 receptors are labelled using 8-OH-DPAT.

The majority of patients with non-ulcerative dyspepsia are, however, not hyperserotoninaemic. Nonetheless, the inventors postulated that altered sensitivity of 5-HT receptors might have similar consequences to high levels of serotonin. It was thus hypothesized that serotonin or serotonergic receptors are supersensitive in non-ulcerative dyspepsia. When an experiment was carried out as hereinafter described to test this hypothesis it was found to be correct in that 70–80% of persons with non-ulcerative dyspepsia were found to have supersensitive serotonin receptors or significant down regulation of $\alpha$-2 noradrenergic receptors in their brains.

Accordingly, it was postulated that the blocking of the serotonin receptors in individuals with non-ulcerative dyspepsia and related conditions would lead to alleviation or reversal of symptoms.

It is an object of the present invention to provide for effective therapy of non-ulcerative dyspepsia and related conditions.

By "related condition" herein is meant inter alia non-ulcerative dyspepsia of the dismotility type, pelvic floor syndrome and oesophageal dyspepsia which have similar symptoms to non-ulcerative dyspepsia. Hereinafter non-ulcerative dyspepsia and said related conditions will be referred to collectively as non-ulcerative dyspepsia.

It is a further object of the present invention to provide a method of diagnosing non-ulcerative dyspepsia which can be carried out without surgical intervention or other invasive method.

SUMMARY OF THE INVENTION

The invention provides a method of treatment of non-ulcerative dyspepsia using cyproheptadine, more particularly non-ulcerative dyspepsia which is characterised by dysfunction of central 5-HT 1A receptors and a method of diagnosing such dysfunction. The latter method is based on an azaspirodecanedione-induced prolactin response.

DETAILED DESCRIPTION OF THE PREFERRED EMBODIMENTS

Figure 1:
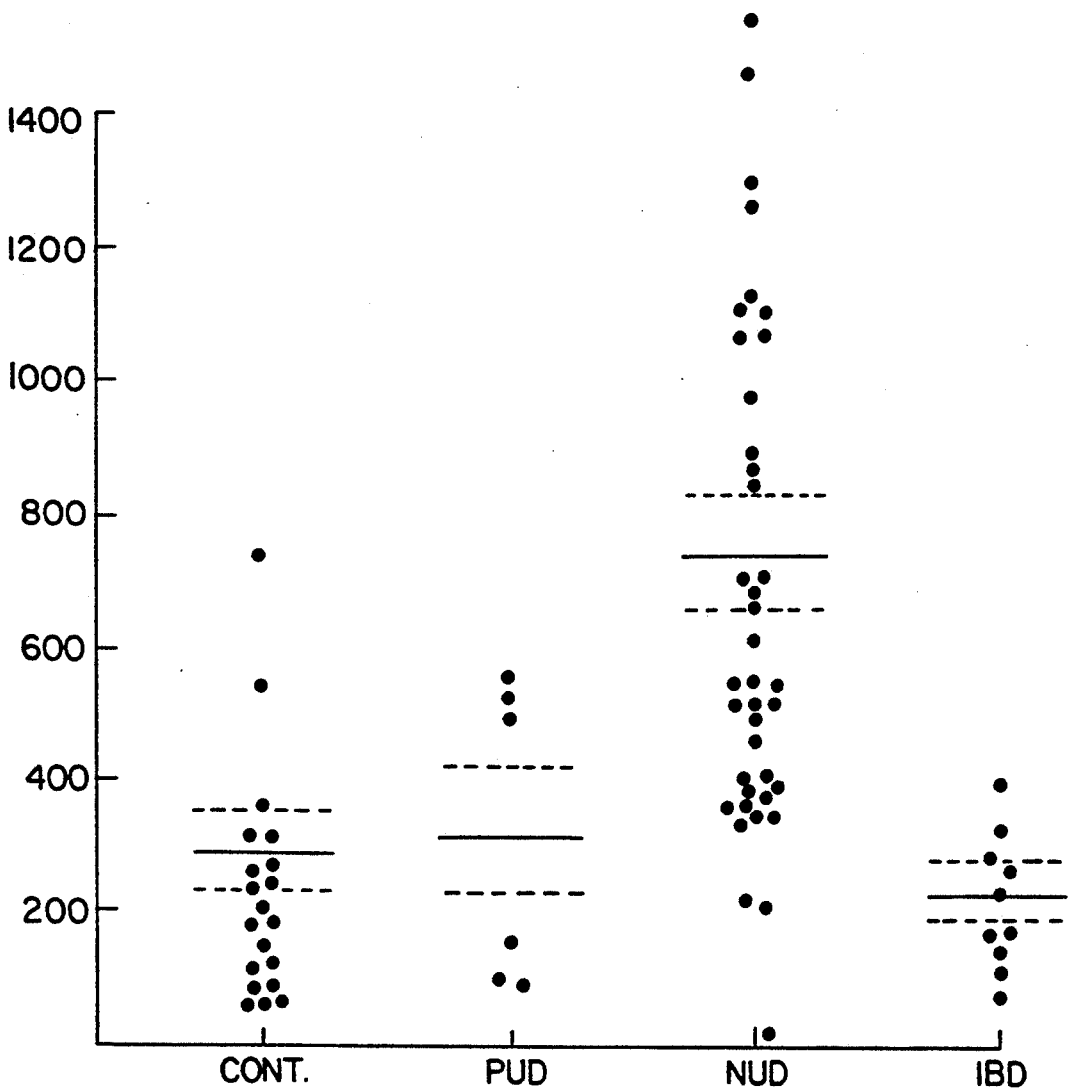

Accordingly, the invention provides a method for the treatment of non-ulcerative dyspepsia in a patient in need of such treatment, which method comprises administering to said patient a therapeutically effective amount of cyproheptadine (4-(5H-dibenzo[a,d] cyclohepten-5-ylidene)-1-methylpiperidine) or a pharmaceutically acceptable salt thereof.

Preferably, the cyproheptadine salt used is the hydrochloride viz cyproheptadine hydrochloride (4-(5H-dibenzo[a,d]cyclohepten-5-ylidene)-1-methylpiperidine hydrochloride sesquihydrate).

The method according to the invention is especially suitable for use in the treatment of non-ulcerative dyspepsia which is characterised by dysfunction of central 5-HT 1A receptors.

Preferably, the central 5-HT 1A receptor dysfunction is diagnosed by an azaspirodecanedione-induced prolactin response. The azaspirodecanedione-induced prolactin response is found to be distinguishable from that observed in a subject with peptic ulcer disease and/or inflammatory bowel disease as hereinafter demonstrated.

It has also been shown that subjects suffering from non-ulcerative dyspepsia exhibit delayed gastric emptying which is directly related to the prolactin response.

The azaspirodecanedione used is suitably buspirone.

Buspirone is a 5-HT 1A agonist/antagonist depending on the state of the receptors.

Other drugs which may be used to elicit the prolactin response are ipsapyrone (Bayer) and Gepirone (Bristol-Myers Squibb Company).

When buspirone is used it is preferably administered to a subject as a single dose of at least 50 mg, more especially 60 mg.

The cyroheptadine active agent is preferably administered orally in an amount of 2-50 mg, more especially 4-20 mg, per day.

The dosage selected will vary in accordance with the requirements of the individual patient as determined by the attending physician.

The active agent can be administered in accordance with the invention as a single dosage or in several partial dosages provided in accordance with the dosage plan as determined by the physician according to the requirements of the patient.

Suitable formulations for oral administration include for example, solid oral dosage forms such as capsules, tablets, coated tablets, dragees, pills, powders and granulates and liquid oral dosage forms such as solutions, syrups, suspension and elixirs.

Earlier work carried out by the inventors pointed to significant abnormalities in noradrenergic activity centrally in non-ulcerative dyspepsia. The precise relationship between noradrenaline and serotonin in non-ulcerative dyspepsia is uncertain. Although not wishing to be bound by any theoretical explanation of the invention, based on our experimental findings, it was postulated that pharmacological manipulation of non-ulcerative dyspepsia leading to improvement was more likely to be produced by the use of a drug which decreases functional activity of serotonin receptors rather than a pharmacological action on the noradrenergic receptors. Cyroheptadine has been found to exhibit such activity.

The invention also provides an in vitro method for the diagnosis of non-ulcerative dyspepsia in a subject suspected of having non-ulcerative dyspepsia, which method comprises identifying in said subject a dysfunction of central 5-HT 1A receptors characterised by the subject's response to azaspirodecanedione-induced prolactin production by estimating the level of prolactin in a sample of blood or a blood fraction obtained from said subject, with the proviso that when the subject is a menstruating female, the diagnosis is carried out in the follicular phase of menstruation.

The azaspirodecanedione is preferably buspirone which is administered as a single dose in an amount of at least 50 mg, more especially 60 mg.

However, as indicated above other more selective 5-HT 1A acting drugs may also be used to obtain increased sensitivity and to minimize side effects.

The blood fraction is preferably plasma.

Preferably, the prolactin response is shown to be distinguishable to that observed in a subject suffering from peptic ulcer disease and/or irritable bowel disease when subjected to the same diagnosis.

Patients with non-ulcerative dyspepsia have also been shown by the inventors to exhibit delayed gastric emptying which is directly related to the prolactin response.

The prolactin response is suitably measured by enzyme immunoassay or radio immunoassay.

The immunoassay methods in accordance with the invention may be carried out using any known format, such as, for example, beads, dipsticks, membranes, particles, plates, rods, strips, etc.

For example, insolubilised or solid phase antibody as used in accordance with the invention is suitably bound to a bead, dipstick, membrane, plate, particle, rod, tube, well, or the like of plastics material or glass in a manner known per se.

More specifically, the insolubilised form of the antibody comprises said antibody absorbed on a surface adapted for protein absorption. The surface may be a bead, membrane, particle, plate rod, tube, well or the like and of a material as hereinbefore specified.

Suitably the surface comprises a plastics microtitration plate or strip adapted for protein adsorption wherein the immunochemical reaction and the estimation of the prolactin can take place, following capturing of the prolactin or release of the prolactin on the insolubilised form of the antibody, depending on the method used.

The relevant surface may be coated directly with an optimum dilution of monoclonal antibody or polyclonal antibody.

The estimation of the bound prolactin derived from the sample can be carried out by enzymatic, fluorometric, luminometric or radiometric assay, using enzymes, fluorochromes, light-emitting probes or radio labels, respectively.

The labelled agents for use in the assays according to the invention are prepared in conventional manner or are purchased from appropriate suppliers. Such labelled agents are normally in the form of conjugates such as enzyme-labelled antibodies for use in competative binding assays. The labelled agent is also suitably an antibody covalently linked to a radio label for use in a radiometric assay.

The invention also provides a test kit or pack for carrying out the in-vitro method hereinbefore specified and which includes an amount of said azaspirodecanedione for administering to one or more subject(s) being investigated for non-ulcerative dyspepsia and sufficient to elicit a prolactin response characteristic of central 5-HT 1A receptor dysfunction.

Preferably, said kit or pack includes the necessary components/ingredients for carrying out the prolactin estimation.

Such a test kit or pack may include antibody coated tubes containing all of the necessary components for carrying out the method according to the invention when a sample of blood or a blood fraction is added thereto. Alternatively, one may provide a tube containing an antibody-enzyme conjugate to which one adds a sample of blood or a blood fraction, which tube is used with an antibody-coated dipstick for a competitive enzyme immunoassay.

BRIEF DESCRIPTION OF THE ACCOMPANYING DRAWINGS

Figure 2:
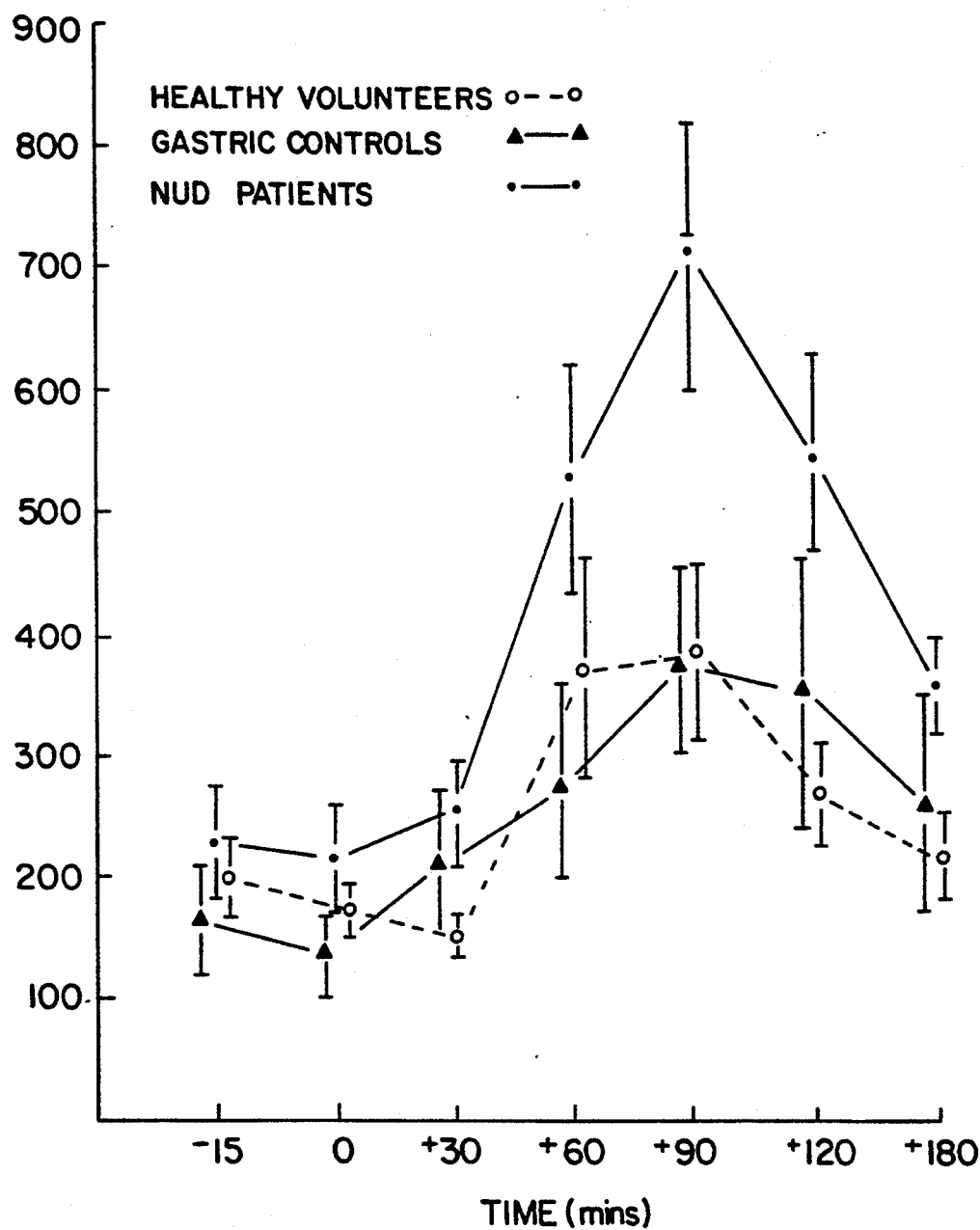
Figure 3:
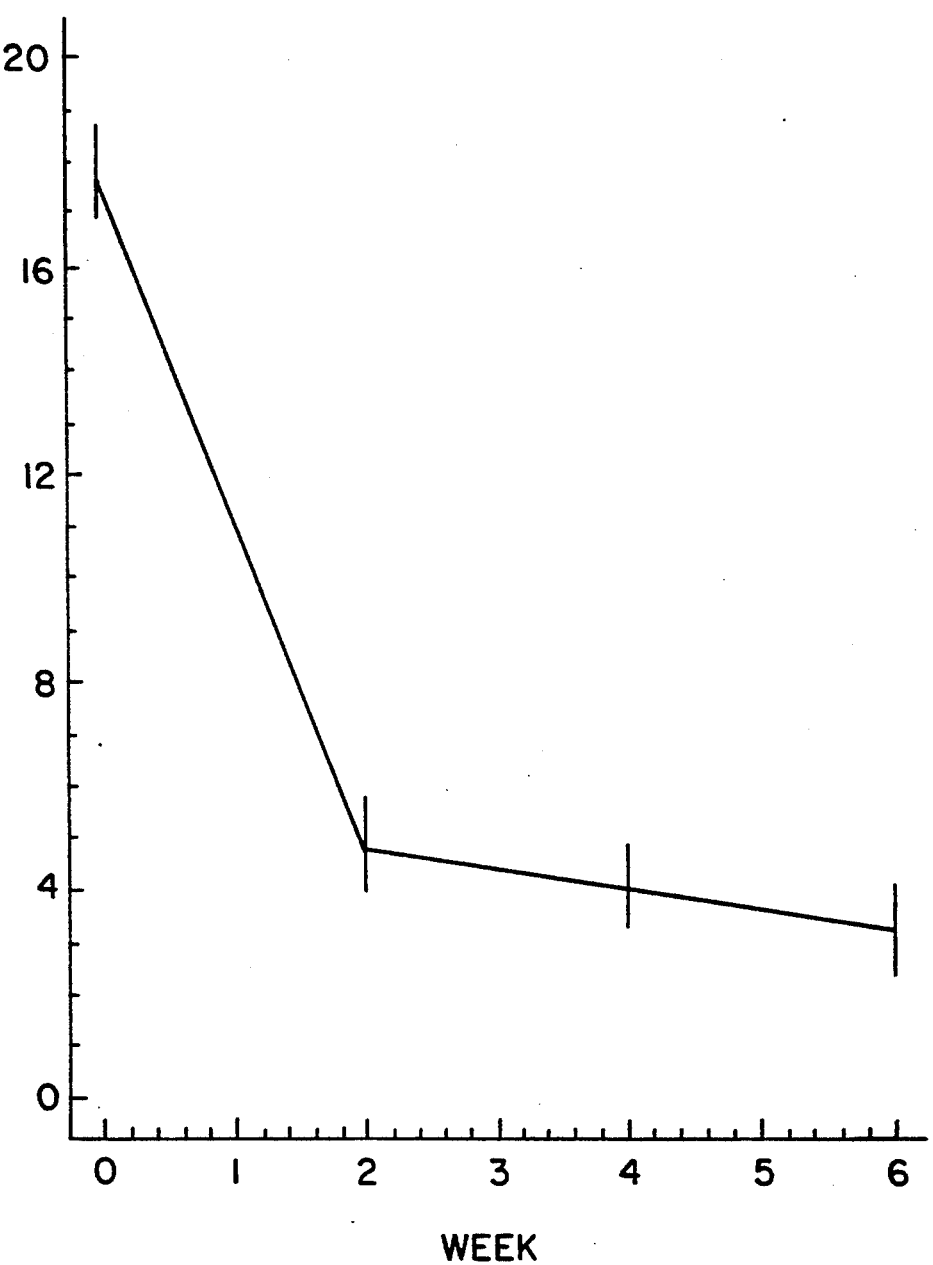

FIG. 1 is a graph of peak (Δ) prolactin response (mU/l) following administration of buspirone in non-ulcerative dyspepsia patients relative to peptic ulcer/gastric controls, inflammatory bowel disease controls and healthy volunteers as described in Example 1;

FIG. 2 is a graph of mean plasma prolactin concentration (mU/l) versus time after administration (min.) following administration of buspirone in non-ulcerative dyspepsia patients relative to gastric controls and healthy volunteers as described in Example 1; the bar represents ±1 standard error; and FIG. 3 is a graph of GSRS total symptom scores in patients with non-ulcerative dyspepsia treated with cyproheptadine as described in Example 2.

EXAMPLE 1

Determination of the Sensitivity of Serotonin Receptors in Non-Ulcerative Dyspepsia As indicated above it was hypothesized that serotonin receptors are supersensitive in non-ulcerative dyspepsia (NUD). An experiment was designed to explore this hypothesis by using prolactin response to buspirone challenge as an index of serotonin receptor sensitivity. It is generally accepted that prolactin release is partially under serotonin control. Buspirone stimulates 5-HT 1A receptors and increases prolactin release.

Thirty nine patients with a diagnosis of NUD, twenty healthy controls, six patients with peptic ulcer disease and ten patients with inflammatory bowel disease (IBD) took part in the study (only male patients were included to exclude variance caused by menstrual hormone fluctuation). All gave written informed consent. Patients with NUD fulfilled the following criteria. They had at least four of the following symptoms for more than three months: early satiety, post-prandial fullness, post-prandial bloating, belching, epigastric pain or heartburn. Endoscopic examination and ultrasound were normal and gastric biopsies were campylobacter negative as this may cause chronic antral gastritis. No other illness was present and patients were drug free for at least three months.

Subjects presented fasting at 8.30 a.m. A cannula was inserted in a forearm vein and the subject was allowed to relax for 15 min. before the first sample of blood was collected (8 ml in a heparinized tube). A second sample was taken 15 min. later at which stage the patient was given an oral dose of buspirone 60 mg. Further blood for prolactin estimation was taken at 60, 90, 120, and 180 min. intervals. Prolactin was measured blind to diagnosis using a fluoroimmunoassay (LKB method; Lovgren, T. et al., 1985, In Collins, W.P. (eds). Alternative immunoassays, John Wiley & Sons Ltd.).

The thirty nine patients with NUD had higher prolactin baselines than controls but such differences do not reach statistical significance. When response to buspirone was determined by measuring either the difference between the baseline and peak values or area under the curve, considerably greater prolactin responses were found in NUD than in the healthy controls, PUD patients or IBD patients (FIG. 1). The mean (+SEM) increase in plasma prolactin following buspirone in NUD was 710.0±73.0 mU/l in contrast to healthy controls with 295.0±86.0 mU/l and PUD patients with 324.0±91.0 mU/l (1-way ANOVA, $F=4.37$, $p<0.05$; NUD v healthy controls, $t=2.58$, $df=57.0$, $p<0.02$). Differences between the response of NUD patients and controls became apparent around 60 min. post-buspirone and reach a peak at 90 min. (FIG. 2).

Central serotonin receptors are considerably more sensitive when stimulated in NUD than in healthy controls. The anxiolytic buspirone was used in the present study to stimulate such receptors. Although not entirely specific for serotonin receptors (it does have an action on dopamine receptors as well) there is sufficient evidence to indicate that its mediation of prolactin release is via the serotonin receptor and can be blocked with the serotonin antagonist methysergide. Buspirone provides the most acceptable method of 5-HT stimulated prolactin release currently available. Responses to it were on average over 100% greater in NUD patients than in healthy controls.

These results provide further evidence of the view that NUD is not a "functional" disorder but one characterised by neurochemical dysfunction in the central nervous system.

EXAMPLE 2

Psychiatric Assessment of Patients with Non-Ulcerative Dyspepsia

A neuroendocrine study carried out indicated that a high percentage of patients with non-ulcerative dyspepsia show blunting of central noradrenergic α-2 responses. Such blunting has also been observed in depression. A study was therefore carried out to investigate dexamethasone responses in patients with NUD to determine if abnormality in this test resembled findings in depression.

A total of forty patients (25 female and 15 male) between the ages of eighteen and fifty years referred to the Gastroenterology Clinic at St. James's Hospital (Dublin) and having a diagnosis of NUD were recruited. They each had both abdominal pain and disordered bowel habit for at least three months. Exclusion criteria included any abnormality on routine haematology, biochemistry including liver function tests and sigmoidoscopy.

All patients were assessed by a consultant psychiatrist and a full psychiatric history and mental state examination were obtained. DSM-III criteria were employed in diagnosis (APA, 1980 supra). The DST was carried out according to the method of Carroll, B. (Brit. J. Psychiatry, 1982; 140: 292-304). Briefly patients were given 1 mg of dexamethasone at 10 p.m. and blood was taken for cortisol examination at 4 p.m. the following day. Cortisol was measured using a radio immunoassay (CIS International). A cortisol level above 137 nmol/l was regarded as non-suppression.

Twenty percent of the sample (8 of 40) were found to have evidence of psychiatric illness, five were depressed (4 female/1 male), two had generalized anxiety states (both female) and one male had panic disorder. None had previously seen a psychiatrist but three were currently being treated by their GPs, one with an antidepressant and two with benzodiazepines. One of the five depressed patients fulfilled criteria for psychotic depression. Four of the total sample gave a family history of affective disorder, three of these were currently depressed and one was free of psychopathology.

Five patients were DST non-suppressors. Of these three were depressed and two were without evidence of psychiatric illness.

The tendency to link NUD with psychiatric illness rather than other illnesses seen in gastroenterology is strong (Chaudhury and Truelove, 1962 supra). The present investigations were conducted to determine if NUD is a variant of affective disorders. The results do not support such a hypothesis. We have found far lower levels of psychopathology in this population than previously described (Chaudhury and Truelove, 1962 supra; Gomez and Dally, 1977 supra). Perhaps this is due to the fact that much of the earlier research in the area used psychiatric diagnoses which were not operationally defined. Our patients were diagnosed in accordance with DSM-III criteria.

Gomez and Dally (1977 supra) noted the fact that many of their patients showed high levels of somatisation and were unable to describe their feelings except in terms of pain, a finding which was not related to level of education. If one assumes that such patients are typical depressives with a tendency to somatise, a far greater level of DST non-suppression would be expected. Overall in the sample nonsuppression rates were only marginally higher than that seen in the general population (Coppen, A. et al, British Journal of Psychiatry 1983, 142, 498–504). The majority of patients did not have a past history or family history of psychiatric illness. It is generally agreed that many patients with affective disorder have a genetic predisposition thereto (Gershon, E. In: Psychiatry Update 1983, Vol 2, L. Grinspoon (ed.), Washington D.C.: APA). If patients with NUD are indeed psychiatrically ill as many previous studies suggest, it is surprising that so few have a family history of affective disorder or other psychiatric illness.

It would thus seem that NUD patients are less psychiatrically ill than previously indicated. The current findings in conjunction with our recent observation demonstrate that up to 70% of patients have blunted noradrenergic α-2 responses and would suggest that such patients have a unique endocrine profile, different from that seen in depression.

EXAMPLE 3

Cyproheptadine in the Treatment of Non-Ulcerative Dyspepsia

A study was carried out to determine the efficacy of cyproheptadine in the treatment of non-ulcerative dyspepsia. All patients who met the inventors' operational criteria for a diagnosis of non-ulcerative dyspepsia were studied. They must have had at least four of the following symptoms for three months: abdominal pain, early satiety, post-prandial fullness, post-prandial bloating, borborygmus, belching, heartburn, or alteration of bowel habit. Patients were excluded if they had any evidence of a) endoscopic or X-ray evidence of structural GIT abnormality, b) campylobacter infection, c) endocrine disorder, d) collagen disease, e) somatic myopathy and f) alcohol abuse.

Thirty patients who met the above described criteria took part in the study. After obtaining an informed consent, each subject was rated on a 15 item GSRS scale for the severity of dyspeptic symptoms. The GSRS scale is a rating scale for the symptoms of gastrointestinal disorders. Following this, each subject was prescribed 4 mg of cyproheptadine hydrochloride daily for a period of one week. Thereafter the dosage was increased as required up to a maximum of 20 mg/day depending on the severity of the symptoms. Subjects were reassessed at the end of weeks 2,4 and 6 using GSRS, and any side effects reported were noted.

Twenty two out of thirty patients had significant reductions in their GSRS scores at the end of 2 weeks, and this improvement was maintained at 6 weeks. Most subjects reported feeling better within hours of commencing cyproheptadine, and, in fact twenty of the twenty two that improved had virtually no symptoms at the end of 6 weeks. The results are shown in FIG. 3.

Over 20 years ago Warner, R.P. (supra) hypothesized that hyperserotoninaemia was the basis of "functional" abdominal pain in some patients. Our results add weight to his hypothesis and indicate that a similar mechanism might operate in those patients with normal serotonin who have supersensitive receptors.

EXAMPLE 4

Abnormal Forebrain Noradrenergic α-2 Receptor Functioning in Patients with Delayed Gastric Emptying.

The involvement of central forebrain α-2 receptors located in the hypothalamus (arcuate nucleus) was examined in a group of patients with delayed gastric emptying (DGE) by measuring serum growth hormone (GH) responses to desipramine. Desipramine normally increases GH level by blocking the reuptake of noradrenaline and indirectly stimulating central α-2 receptors. GH release factor is produced at the arcuate nucleus after stimulation. GH responses were studied in eight patients with DGE and in ten healthy controls. Patients with organic pathology and receiving medication were excluded.

Both patients and controls presented fasting at 8:30 a.m. An 18G cannula was inserted in a forearm vein. The subject was then allowed to relax for 20 min. before blood was taken for GH estimation. Two baseline 8 ml samples were collected at a 15 min. interval in lithium-heparin tubes. Subjects remained fasting for the duration of the test but were not allowed to sleep. A dose of desipramine 1 mg/kg body weight was given orally. Blood for further GH estimation was collected 90,120 and 180 min. following the administration of desipramine. GH was assayed (blind to diagnosis) by a double antibody radio immunoassay (Salvatore, R., In: Laron and Butenandt (eds.) *Evaluation of Growth Hormone Secretion*, Basel: Karger 1983). Responses were regarded as blunted if GH levels failed to rise at least 5 mU/l above baseline values. Furthermore DGE was determined by isotopic (Tc99) scintigraphy of a standard solid meal.

The mean GH response in DGE patients was significantly ($p<0.05$) lower than in the controls. Six of the eight patients had blunted responses. The results suggest the presence of abnormal forebrain α-2 receptor functioning in patients with DGE.

Central noradrenergic functioning in IBS was also assessed using a desipramine challenge test as described in Example 4. Of thirteen pateints with IBS, eleven showed blunting indicative of abnormal central α-2 functioning in IBS (Dinan, T.G., et al 1990, Journal of Psychosomatic Research 34 No. 5, 575–580).

A direct correlation has been found between the prolactin response described in Example 1 and delayed gastric emptying in subjects with NUD.

What we claim is:

1. A method for the treatment of irritable bowel syndrome characterized by dysfunction of central 5-HT 1A receptors in a patient in need of such treatment, which method comprises administering to said patient a therapeutically effective amount of cyproheptadine or a pharmaceutically acceptable salt thereof.

2. A method according to claim 1, wherein the central 5-HT 1A receptor dysfunction is diagnosed by an azaspirodecanedione-induced prolactin response.

3. A method according to claim 2, wherein the azaspirodecanedione-induced prolactin response is distinguishable from that observed in a subject with peptic ulcer disease and/or inflammatory bowel disease.

4. A method according to claim 2, wherein the azaspirodecanedione is buspirone.

5. A method according to claim 4, wherein the buspirone is administered to a subject as a single dose of at least 50 mg.

6. A method according to claim 1, wherein the cyproheptadine is administered orally.

7. A method according to claim 6, wherein the cyproheptadine is administered in an amount of 4–20 mg/day.

8. A method according to claim 1, wherein said pharmaceutically acceptable salt is cyproheptadine hydrochloride.

9. A method according to claim 1, wherein the central 5-HT 1A receptor dysfunction is diagnosed by an ipsapyrone-induced prolactin response or a Gepirone-induced prolactin response.

10. A method according to claim 4, wherein the buspirone is administered to a subject as a single dose of 60 mg.

11. A method according to claim 6, wherein the cyproheptadine is administered in an amount of 2–50 mg/day.

12. A method according to claim 11, wherein the cyproheptadine is administered in a single dose, or in several partial doses.

13. A method according to claim 6, wherein the cyproheptadine is administered in a formulation selected from the group consisting of a solid oral dosage form selected from the group consisting of a capsule, a tablet, a coated tablet, a dragée, a pill, a powder, and a granulate, and a liquid oral dosage form selected from the group consisting of a solution, a syrup, a suspension, and an elixir.

* * * * *

UNITED STATES PATENT AND TRADEMARK OFFICE
CERTIFICATE OF CORRECTION

PATENT NO. : 5,324,738

DATED : June 28, 1994

INVENTOR(S) : Timothy G. Dinan et al.

It is certified that error appears in the above-identified patent and that said Letters Patent is hereby corrected as shown below:

On the title page, item:

-- [30]  Foreign Application Priority Data

September 20, 1989 [IR]  Ireland .............. 2019/89--

Signed and Sealed this

Twenty-fourth Day of January, 1995

Attest:

BRUCE LEHMAN

Attesting Officer     Commissioner of Patents and Trademarks